(12) United States Patent
Kelly et al.

(10) Patent No.: US 12,144,352 B2
(45) Date of Patent: Nov. 19, 2024

(54) DRY SHAMPOO HEAD LICE TREATMENT

(71) Applicant: Kelly Green Living Ltd, Bury (GB)

(72) Inventors: Rachel Kelly, Bury (GB); Joanna Kelly, Bury (GB)

(73) Assignee: Kelly Green Living, LTD, Bury (GB)

( * ) Notice: Subject to any disclaimer, the term of this patent is extended or adjusted under 35 U.S.C. 154(b) by 651 days.

(21) Appl. No.: 17/257,737

(22) PCT Filed: Jul. 9, 2019

(86) PCT No.: PCT/GB2019/051927
§ 371 (c)(1),
(2) Date: Jan. 4, 2021

(87) PCT Pub. No.: WO2020/012171
PCT Pub. Date: Jan. 16, 2020

(65) Prior Publication Data
US 2021/0267211 A1   Sep. 2, 2021

(30) Foreign Application Priority Data

Jul. 9, 2018 (GB) ..................... 1811233

(51) Int. Cl.
*A01N 59/00* (2006.01)
*A01N 43/16* (2006.01)
*A01N 65/40* (2009.01)
*A01N 65/44* (2009.01)

(52) U.S. Cl.
CPC ............ *A01N 59/00* (2013.01); *A01N 43/16* (2013.01); *A01N 65/40* (2013.01); *A01N 65/44* (2013.01)

(58) Field of Classification Search
None
See application file for complete search history.

(56) References Cited

U.S. PATENT DOCUMENTS 5,763,500 A * 6/1998 Roulier .................... A61K 8/88
521/149
2011/0118196 A1 5/2011 Chazot
2015/0250166 A1 9/2015 Goldblum et al.
2016/0317396 A1 * 11/2016 Perfitt ................... A45D 33/02
2017/0156344 A1 6/2017 Wakefield

FOREIGN PATENT DOCUMENTS

| CN | 108124874 A1 | | 6/2018 | |
|---|---|---|---|---|
| FR | 2207688 | * | 11/1972 | |
| FR | 3065875 A1 | * | 11/2018 | ........... A61K 8/0241 |
| WO | WO-2018026901 A1 | * | 2/2018 | ............. A01N 35/02 |

* cited by examiner

*Primary Examiner* — Melissa S Mercier
(74) *Attorney, Agent, or Firm* — GableGotwals

(57) ABSTRACT

A dry shampoo composition for treating, deterring and/or killing insect and arachnid infestations, particularly head lice infestations. The composition includes diatomaceous earth and at least one starch.

9 Claims, 4 Drawing Sheets

A diagram of the test set-up for one replicate of irritant testing, in a 14 cm glass Petri dish. The treated and control hair swatches were placed in the center of their respective Petri dish.

View of a fine background layer of Diatomaceous Earth (DE) product (~20mg) rubbed on the forearm prior the positioning of the rearing unit to emulate product application on the scalp.

View of a background layer of Diatomaceous Earth (DE) product (~30mg) rubbed on the mesh end of the rearing unit to emulate product application on the scalp.

View of the rearing units: A) open unit with hair switch, B) above view of a closed unit with hair swatch, C) bottom view of a closed unit with hair swatch.

View of a rearing unit secured on the participant's forearm using clean dressing.

Percentage (%) of head lice at 0, 10, 30, 60 minutes and 3 and 6 hours after exposure to a formulated dry product containing Diatomaceous Earth (DE) on hair swatches treated (A) post lice-infestation (Treatment 1, n=3) or (B) pre lice-infestation (Treatment 2, n=2).

DRY SHAMPOO HEAD LICE TREATMENT

CROSS-REFERENCE TO RELATED APPLICATIONS

This United States application is the National Phase of PCT Application No. PCT/GB2019/051927 filed 9 Jul. 2019, which claims priority to British Patent Application No. 1811233.4 filed 9 Jul. 2018, each of which is incorporated herein by reference.

The invention to which this application relates is to a product or formulation for a natural product based dry shampoo that has any one or any combination of head lice deterrent, repellent and/or insecticidal (including ovicidal and/or adulticidal) properties.

Although the present invention relates to the provision of a dry shampoo for human adults and children that deters, repels and/or treats lice and head lice at one or more stages in their life cycle, the skilled person will appreciate that the invention could be used to deter, repel and/or treat other insect or arachnid infestations in people or animals such as fleas, lice and/or ticks.

In the UK, over two million children under the age of 15 suffer from an infestation of head lice each year. Human head lice (*Pediculus humanus capitis*) are wingless, about 3 mm long (adult louse), six legged, blood-sucking parasites that live on the scalp of humans but not on house pets. The head louse feeds every three to six hours by sucking blood and simultaneously injecting saliva. Head lice cannot survive for more than 24 to 36 hours when off the human body. The Itching may develop as a result from sensitization to components of the saliva and/or allergy to the louse droppings. The life cycle from egg to egg takes 3 to 4 weeks.

Presently many shampoos including insecticides are used for the treatment of head lice, include organochlorines (lindane), organophosphates (malathion), carbamates (carbaryl), pyrethrins (pyrethrum), pyrethroids (permethrin, phenothrin, bioallethrin), and spinosad (spinosyn A and spinosyn D). To date there has been no effective treatment based on natural products or shampoos which do not contain synthetic chemical insecticides.

It is therefore an aim of the present invention to provide a composition for treating head lice infestations which address the abovementioned problems.

It is a further aim of the present invention to provide a method of treating or deterring head lice infestations.

In a first aspect of the invention there is provided a dry shampoo composition for treatment, deterring and/or killing head lice infestations, said composition including diatomaceous earth and at least one starch.

Typically the composition can be used to treat deter or kill insect and/or arachnids on humans or animals, for example lice, fleas and/or ticks.

Typically the starch is a plant based starch or polysaccharide. Further typically the starch is derived from a cereal. The skilled person will appreciate that the at least one starch may be a blend or mix of starches from different sources and/or plants.

Preferably the starch is a powder. Typically the starch is obtained from the endosperm of the kernel of a cereal plant or crop.

In one embodiment at least part of the starch is a corn or maize based starch. Typically the starch includes cornflour. Further typically the starch is a fine powder or mixture of fine powder starches.

In one embodiment the starch includes powder obtained from arrowroot.

Typically the diatomaceous earth has a particle size of 10 to 200 μm. The skilled person will appreciate that diatomaceous earth can have a particle size of less than 3 μm to more than 1 mm. Typically diatomaceous earth has a range of particle sizes however the present invention uses diatomaceous earth which is a fine porous powder.

In one embodiment the composition includes 50-95 wt % diatomaceous earth. In a further embodiment the composition includes 60-75% diatomaceaous earth. Typically the composition includes approximately 60% by weight of diatomaceous earth.

In one embodiment the composition includes 5-50% starch. In a further embodiment the composition includes 10-30 wt % of starch material. Typically the composition includes approximately 20 wt % starch material.

In one embodiment the composition includes approximately 5-15% weight of starch derived from a first type of plant material. Typically the composition includes 5-15% weight derived from a first type of plant material and 5-15% weight derived from a second type of plant material.

In one embodiment the composition includes approximately 5-15 weight of starch material as cornflour. Typically the composition includes approximately 10% weight of starch material as cornflour.

In one embodiment the composition includes approximately 5-15 weight of starch material as arrowroot powder. Typically the composition includes approximately 10% weight of starch material as arrowroot.

In one embodiment the composition includes approximately 5-15 weight of cornflour and 5-15% weight of arrowroot. Typically the composition includes approximately 10% cornflour and 10% arrowroot.

In one embodiment the composition includes approximately 1 to 20 wt of one or more plant and/or herb based powders. Typically the composition includes approximately 1-20% wt, particularly powders derived from non-cereal based plants and/or herbs. Further typically the composition includes approximately any one or any combination of the following powders:

Aloe Vera powder,
Chamomile powder,
Marshmallow root powder,
Nettle root powder, and/or
Horsetail powder In a preferred embodiment the composition includes approximately 10% wt, of powders derived from non-cereal based plants and/or herbs.

In a second aspect of the invention there is provided a method of deterring, repelling and/or killing head lice using a dry shampoo wherein said dry shampoo includes diatomaceous earth and at least one starch, said method including the step of applying the shampoo to the hair and/or scalp of a person.

In a third aspect of the invention there is provided a method of manufacturing a dry shampoo with head lice deterrent, repellent and/or insecticidal (including ovicidal and/or adulticidal) properties said method including the step of mixing or combining diatomaceous earth and at least one starch.

In one embodiment of the invention there is provided diatomaceous earth (food grade) with a mix of botanical plant powders including any one or any combination of; cornflower, arrowroot, nettle, marshmallow, horsetail, dandelion and/or chamomile In one embodiment the composition is white or off whiteish in colour.

In one embodiment the composition includes one or more pigments or colourants. Typically the powder blends in and 'disappears' into the roots/scalp but colour variants for different hair colour could be used.

Further typically the composition is odourless.

In one embodiment the composition includes one or more scents and/or fragranced compounds.

Specific embodiments of the invention are now described with reference to the following figures, wherein.

EXPERIMENTAL

1. Introduction

*Pediculus humanus capitis*, the human head louse, is a blood-sucking insect that has parasitized humans for thousands of years. Despite this long history, head lice infestations remain a public health problem throughout the world, particularly in children. Head lice infestations can have significant socio-economic consequences. Children with head lice infestation can be excluded from school, and carers may have to refrain from going to work if children have to stay at home. Furthermore, *P. capitis* may lead to social exclusion, particularly for children with chronic infestations. Insecticides have been long-used for the control of head lice infections, however, this has led to insecticide-resistant populations worldwide. New methods of control are needed to effectively kill head lice infections.

The objectives of this study were to determine the irritant property and killing efficacy of a novel dry product containing Diatomaceous Earth (DE) and starch against *Pediculus humanus capitis* adult and nymphs in vitro.

2. Materials 2.1. Test Formulations

A formulated dry product containing Diatomaceous Earth (DE) and starch was supplied by Kelly Green Living Ltd.

The product was stored at ambient temperature until they were used in the experiments.

2.2. Test Insects

*Pediculus humanus capitis* (the human head louse) lice were collected in London, UK. A mixture of adults and nymphs were used, and they were examined for activity and morphological integrity under a dissecting microscope before testing. Both female and male head lice were used.

3. Methods 3.1. Irritant Bioassay

All tests were conducted in a testing room at LSHTM maintained at 25±2° C. and 65±10% RH. Hair swatches were made of approximately 300 strands of human hair (approx. 0.5 cm diameter) of uniform length (approx. 8 cm long) and colour, and bound together at one end with a piece of masking tape.

Figure 1:
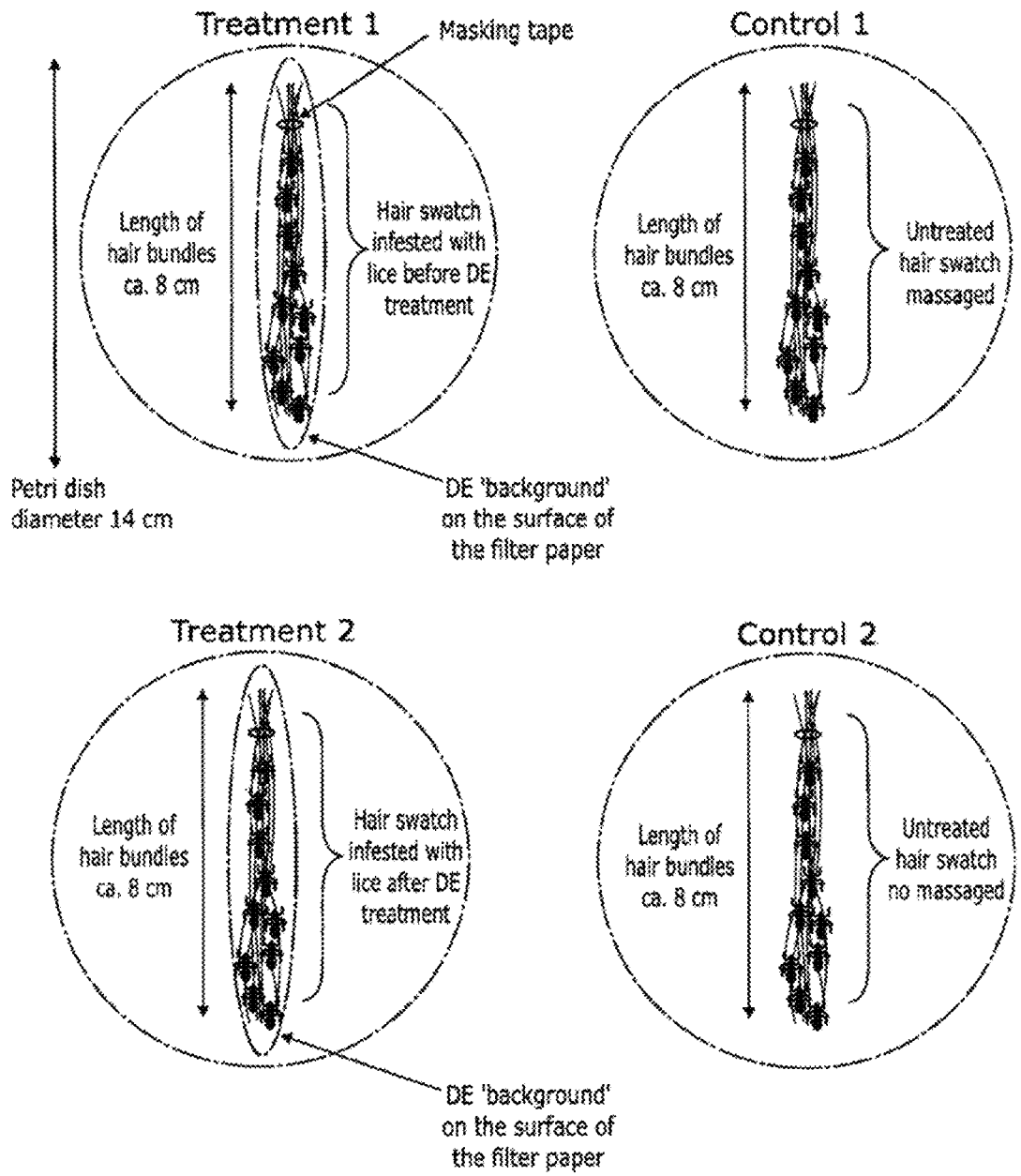
FIG. 1 is a diagram of the test set-up for one replicate of irritant testing, in a 14 cm glass Petri dish. The treated and control hair swatches were placed in the center of their respective Petri dish.

The bioassay set-up is shown in FIG. 1 and consisted of:

Treatment 1: DE treatment post lice-infestation: the hair swatch was infested with 10 healthy head lice. The product (1 g) was then sprinkled onto the hair swatch and the hair swatch was massaged with gloved fingers for 20 seconds.

Control 1: the hair swatch was infested with 10 healthy head lice and the hair swatch was massaged with gloved fingers for 20 seconds. The hair swatch was left untreated.

Treatment 2: DE treatment pre lice-infestation: the product (1 g) was sprinkled onto the hair swatch and then the swatch was infested with 10 healthy head lice.

Control 2: the hair swatch was infested with 10 healthy head lice. No massaging or treatment of the hair occurred.

After treatment (either before or after infestation), the hair swatch was removed from the excess product. The actual amount of DE product applied (in mg) to the treatment hair swatches was assessed by weighing the hair swatch before and after DE treatment.

The hair swatches were then placed into a glass Petri dish (140 mm diameter), which was lined with clean filter paper. In the Petri dishes containing the treatment swatches, ~20 mg of product (i.e. DE background) was applied as a fine layer to the filter paper prior to adding the hair swatch. No product was added to the control Petri dishes.

The number of head lice on each hair swatch was counted after 0, 10, 30, 60 minutes, 3 hours and 6 hours. The vitality of the head lice at each of these time points was also recorded using a dissecting microscope. Lice were classified as:

1: Vital lice (no changes in their levels of activity or behaviour post treatment)

2: Lice with major vital signs (walking but unable to walk in a normal fashion or no reflex when rolled on its back)

3: Lice with minor vital signs (not walking but internal (gut), leg and/or antennae movements present)

4: No vital signs at all (complete absence of any vital signs such as internal (gut), antennae or leg movement with or without forceps stimulation)

Three replicates were completed for Treatment 1 (DE treatment post lice-infestation) and Control 1, whereas two replicates were completed for Treatment 2 (DE treatment pre lice-infestation) and Control 2.

3.2. Wristlet Bioassay

Figure 2:
FIG. 2 is a view of a fine background layer of Diatomaceous Earth (DE) product (~20 mg) rubbed on the forearm prior the positioning of the rearing unit to emulate product application on the scalp.
Figure 3:
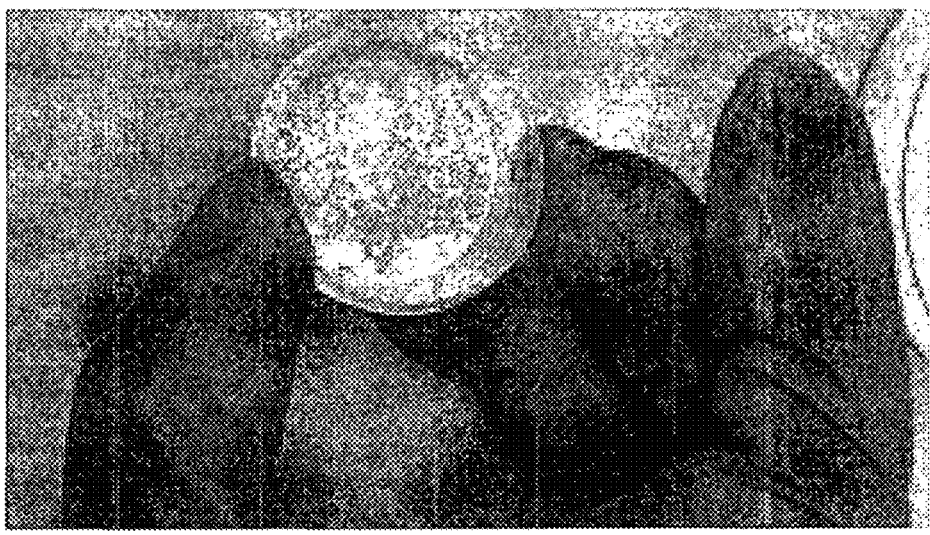
FIG. 3 is a view of a background layer of Diatomaceous Earth (DE) product (~30 mg) rubbed on the mesh end of the rearing unit to emulate product application on the scalp.

Hair swatches were made of approximately 400 strands of human hair (approx. 0.5 cm diameter) of uniform length (approx. 6 cm long) and colour, and bound together at one end with a piece of masking tape. Each dry hair swatch was infested with 10 healthy head lice (mixture of male and female adults and nymphs >2 mm). The hair swatch was then treated (if applicable) and removed from the excess product. The actual amount of DE product applied (in mg)

to the hair swatch was assessed by weighing the hair swatch before and after DE treatment. The bioassay set-up consisted of:

Treatment wristlet: the hair swatch was infested with 10 healthy head lice. The product (1 g) was then sprinkled onto the hair swatch and it was massaged with gloved fingers for 20 seconds. A background layer of DE product was also applied onto the mesh end of the rearing unit (~30 mg) and on the skin area where the wristlet was positioned (~20 mg, FIGS. 2 and 3).

Control wristlet: the hair swatch was infested with 10 healthy head lice and it was massaged with gloved fingers for 20 seconds. The hair swatch, rearing unit and skin were left untreated.

Figure 4:
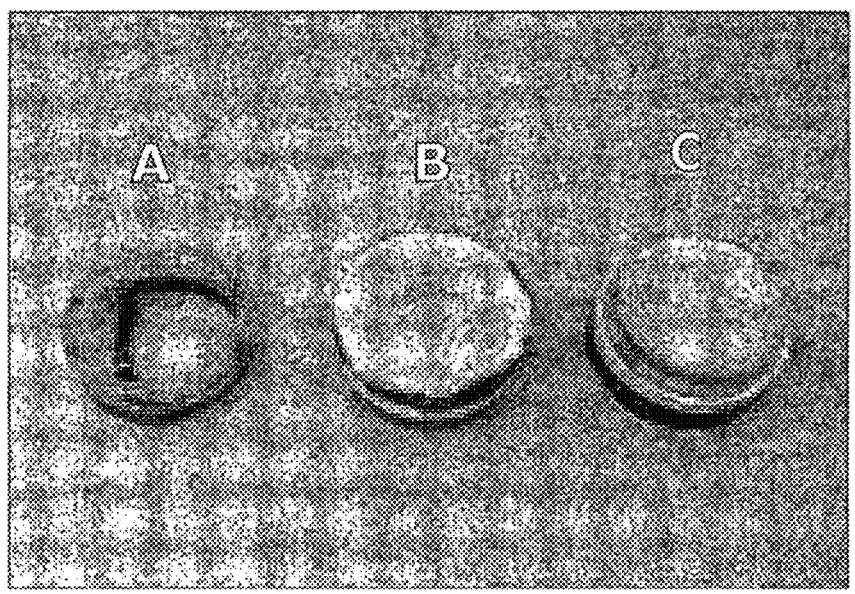
FIG. 4 is a view of the rearing units: A) open unit with hair swatch, B) above view of a closed unit with hair swatch, C) bottom view of a closed unit with hair swatch)

One infested hair swatch was placed inside a rearing unit/wristlet (4 cm diameter) sealed with fine mesh on each end (FIG. 4). All tests were conducted on the forearms of members of staff. This semi in-vivo set-up allowed the head lice to feed ad libitum during the whole duration of the bioassay.

Figure 5:
FIG. 5 is a view of a rearing unit secured on the participant's forearm using clean dressing.

The position of the rearing unit was randomised between test runs (Table 1). The rearing units were placed on a different forearm to avoid cross contamination. The rearing unit was secured using microporous tape and a clean dressing (FIG. 5). The participant's forearms remained dry during the bioassay.

TABLE 1

Randomisation schedule

| Replicate | Participant ID | Left forearm | Right forearm |
|---|---|---|---|
| 1 | CRx | DE treated | Control |
| 2 | CR | Control | DE treated |
| 3 | CRx | DE Treated | Control |
| 4 | CRx | Control | DE treated |
| 5 | CR | Control | DE treated |

The vitality of the head lice was assessed after 0, 24 hours and 48 hours under a dissecting microscope as described on the vitality scale presented in section 3.1. Irritant bioassay. Five replicates were completed.

4. Results 4.1. Irritant Bioassay

On average 20 mg±6 mg of DE product was added to hair swatches for Treatment 1 (DE treatment post lice-infestation) whereas 15 mg±7 mg of DE product was added to hair swatches for Treatment 2 (DE treatment pre lice-infestation).

4.1.1. Irritancy

Figures 6A, 6B:
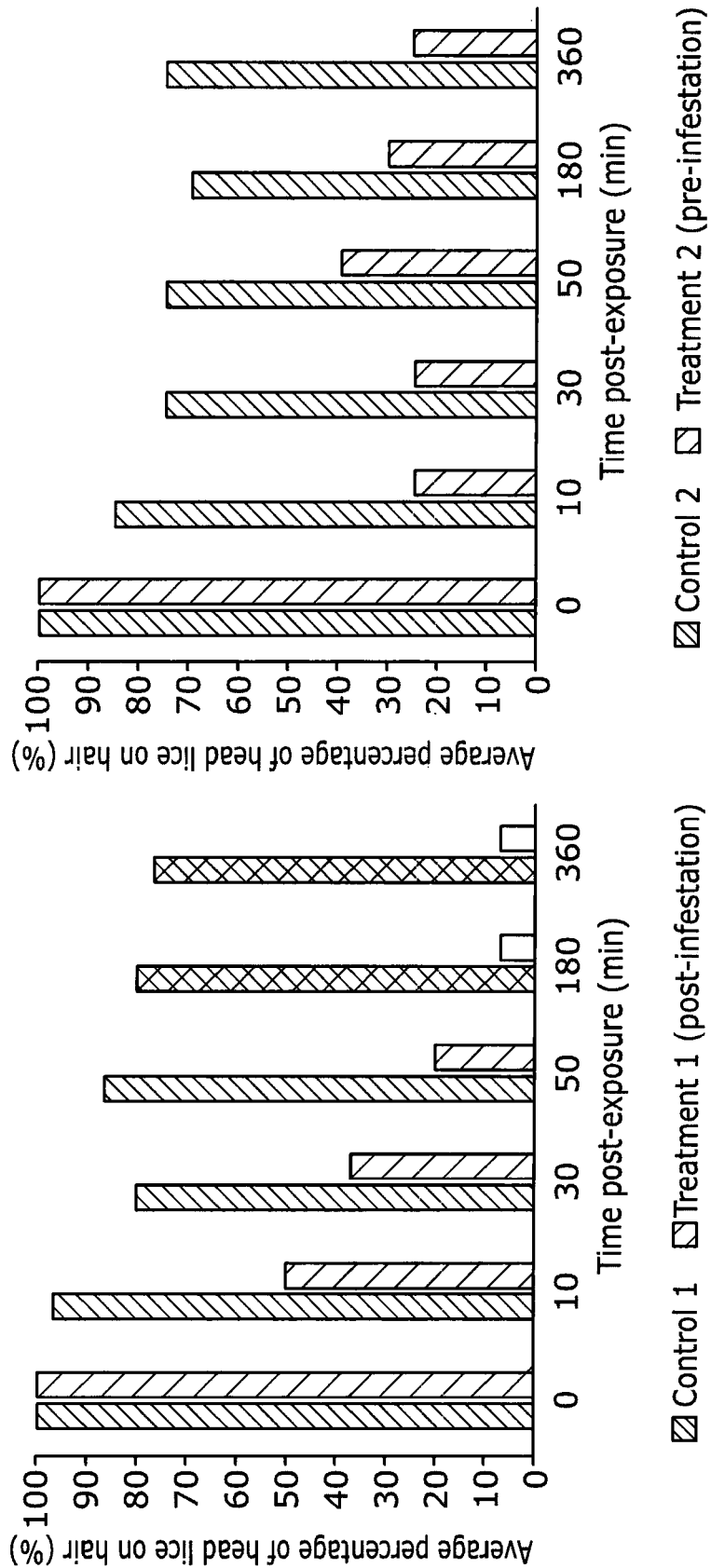
FIG. 6 is a graph of Percentage (%) of head lice at 0, 10, 30, 60 minutes and 3 and 6 hours after exposure to a formulated dry product containing Diatomaceous Earth (DE) on hair swatches treated (A) post lice infestation (Treatment 1, n=3) or (B) pre lice-infestation (Treatment 2, n=2).

Ten minutes after exposure, 50% of head lice which were exposed to the DE product whilst on the hair swatch (Treatment 1, DE treatment post lice-infestation) remained on the hair swatches (FIG. 6A). The number of head lice which remained on the hair swatches which were treated with DE post lice infestation (Treatment 1) reduced over time (FIG. 6A). Only 7% of head lice remaining on the hair swatches after 6 hours. With the control hair swatches (Control 1), more than 77% of head lice remained on the hair swatches over the course of the bioassay (FIG. 6A).

Ten minutes after exposure, 25% of head lice which were infested onto a DE treated hair swatches (Treatment 2, DE treatment pre lice-infestation) remained on the hair swatches (FIG. 6B). The number of head lice remaining on the hair swatches which were treated with DE pre lice-infestation (Treatment 2) increased to 40% 1 hour after exposure (FIG. 6B) but this reduced to 25% 6 hours after exposure to DE product. With the control hair swatches (Control 2), more than 70% of head lice remained on the hair swatches over the course of the bioassay (FIG. 6B).

4.1.2. Vital Signs

Three hours after treating the hair swatches with DE post lice-infestation (Treatment 1), 60% of the head lice showed minor or no vital signs and 37% of head lice shown no vital signs (Table 2 and 3). Six hours after exposure, this increased to 90% of head lice showing minor or no vital sign and 87% showing no vital signs (Table 2 and 3).

Three hours after lice were exposed to hair swatches pre-treated with DE (Treatment 2), 10% of the head lice showed minor or no vital signs and 5% showed no vital signs (Table 2 and 3). Six hours after exposure, this increased to 50% showing minor or no vital sign and 30% showing no vital signs (Table 2 and 3).

With the control hair swatches not exposed to DE product but massaged after infestation (Control 1), 3% of the head lice showed no vital signs from 1 hour post exposure to the end of the bioassay (Table 2 and 3). Similarly, 5% of the head lice on hair swatches not exposed to DE product and not massaged (Control 2) showed minor or no vital signs 3 hours from the start of the bioassay until the end (Table 3 and 4).

TABLE 2

Percentage (%) of head lice scoring 3 (Lice with minor vital signs) and 4 (no vital signs) at 10, 30, 60 minutes and 3 and 6 hours after exposure to a formulated dry product containing Diatomaceous Earth (DE).

| | | Time point post exposure | | | | |
|---|---|---|---|---|---|---|
| | T0 | +10 min | +30 min | +1 hr | +3 hr | +6 hr |
| Control 1 | 0 | 0 | 0 | 3% | 3% | 3% |
| Treatment 2 (post-infestation) | 0 | 0 | 0 | 3% | 60% | 90% |
| Control 2 | 0 | 0 | 0 | 0% | 5% | 5% |
| Treatment 2 (pre-infestation) | 0 | 0 | 0 | 0% | 10% | 50% |

TABLE 3

Percentage (%) of head lice scoring 4 (no vital signs) at 10, 30 and 60 minutes and 3 and 6 hours after exposure to a formulated dry product containing Diatomaceous Earth (DE).

| | | Time point post exposure | | | | |
|---|---|---|---|---|---|---|
| | T0 | +10 min | +30 min | +1 hr | +3 hr | +6 hr |
| Control 1 | 0 | 0 | 0 | 3% | 3% | 3% |
| Treatment 2 (post-infestation) | 0 | 0 | 0 | 0% | 37% | 87% |
| Control 2 | 0 | 0 | 0 | 0% | 0% | 5% |
| Treatment 2 (pre-infestation) | 0 | 0 | 0 | 0% | 5% | 30% |

4.2. Wristlet Bioassay

On average hair swatches were treated with 40 mg±12 mg of DE product.

4.2.1. Vital Signs

Twenty-four hours after treating the hair swatches, 100% of the head lice showed no vital signs and there was no head lice with minor vital signs. Therefore, the bioassay was stopped at 24 hours and only the data of the head lice scoring 4 were presented (Table 4). With the control wristlet, 38% of the head lice showed no vital signs at 24 hours (Table 4).

TABLE 4

Percentage (%) of head lice scoring 4 (no vital signs) at 0, 24 and 48 hours after exposure to a formulated dry product containing Diatomaceous Earth (DE).

| Treatment | Time point post exposure | | |
|---|---|---|---|
| | T0 | +24 hr | +48 hr |
| Control wristlet | 0% | 38% | — |
| Treatment wristlet | 0% | 100% | — |

5. Conclusion

5.1. Irritant Bioassay

Hair swatches were either infested with head lice and then treated with DE or hair swatches were treated with DE and then infested with head lice, in vitro. Ten minutes after exposure, 50% or 25% of head lice remained on the hair swatches which had been treated post lice-infestation or treated pre lice-infestation respectively. Three hours after exposure, this was reduced to 7% and 25% respectively. In the control hair swatches more than 70% of head lice remained on the hair swatch for the whole duration of the irritant bioassay.

Treatment with DE of hair swatches post lice-infested caused 87% mortality within 6 hours after exposure, whereas treatment with DE of hair swatches pre lice-infestation caused 30% mortality within 6 hours after exposure.

The low head lice mortality (3-5%) observed in the controls was largely due to the desiccation and starvation of the insects during the bioassay. It should be noted that only 2-3 replicates were conducted and testing was done in vitro.

5.2. Wristlet Bioassay

Hair swatches were infested with head lice and enclosed inside a rearing unit allowing the head lice to feed on fresh blood during the duration of the bioassay. When DE product was applied to hair swatches and the testing area (i.e. skin and wristlet netting), 100% of the head lice were killed within 24 hours after exposure.

Some head lice in the in control wristlet showed no vital signs at 24 hours (38% mortality) despite the access to fresh blood ad libitum. This mortality in the control was largely due to the desiccation and starvation of few head lice that could not adapt to the semi in-vivo conditions created by the wristlet.

The invention claimed is:

1. A dry shampoo composition that effectively deters, repels, and/or kills head lice, said composition consisting only of diatomaceous earth and approximately 5-50 wt % corn flour.

2. A composition according to claim 1 wherein the diatomaceous earth has a particle size of 10 to 200 μm.

3. A composition according to claim 1 wherein the composition includes 60-75 wt. % diatomaceous earth.

4. A composition according to claim 1 wherein the composition includes approximately 5-15 wt % of corn flour.

5. A composition effective for deterring, repelling, and/or killing headlice and consisting only of diatomaceous earth, corn flour, and 5-15% weight of arrowroot powder.

6. A composition according to claim 5 wherein the composition includes approximately 5-15% weight of corn flour.

7. A composition according to claim 6 wherein the composition includes approximately 10% cornflour and 10% arrowroot powder.

8. A composition effective for deterring, repelling, and/or killing headlice and consisting only of diatomaceous earth, corn flour, and approximately 1 to 20% wt of one or more of the following non-cereal plant and/or herb based powders:
   Arrowroot powder;
   Dandelion powder,
   Aloe Vera powder,
   Chamomile powder,
   Marshmallow powder;
   Marshmallow root powder,
   Nettle powder;
   Nettle root powder, and/or
   Horsetail powder.

9. A method to deter, repel and/or kill head lice using a dry shampoo, said method comprising the step of applying the dry shampoo consisting only of diatomaceous earth and 5-50 wt % corn flour to the hair and/or scalp of a person.

* * * * *